(12) United States Patent
Ariav

(10) Patent No.: US 7,081,683 B2
(45) Date of Patent: Jul. 25, 2006

(54) METHOD AND APPARATUS FOR BODY GENERATION OF ELECTRICAL ENERGY

(76) Inventor: Arie Ariav, 122 Kochav Michael, 79 304 Doar Na Hof Ashkelon (IL)

( * ) Notice: Subject to any disclaimer, the term of this patent is extended or adjusted under 35 U.S.C. 154(b) by 122 days.

(21) Appl. No.: 10/627,738

(22) Filed: Jul. 28, 2003

(65) Prior Publication Data

US 2004/0021322 A1   Feb. 5, 2004

Related U.S. Application Data

(60) Provisional application No. 60/399,416, filed on Jul. 31, 2002.

(51) Int. Cl.
*A61B 5/02* (2006.01)
*H02P 9/04* (2006.01)

(52) U.S. Cl. .................. 290/1 R; 600/481; 600/488

(58) Field of Classification Search ............... 290/1 R; 300/338, 339; 604/97.02; 368/64; 60/399, 60/406; 600/481, 485, 486, 488, 500, 502, 600/534, 561
See application file for complete search history.

(56) References Cited

U.S. PATENT DOCUMENTS

| | | | | |
|---|---|---|---|---|
| 3,456,134 A | * | 7/1969 | Ko ........................... 607/35 |
| 3,486,506 A | * | 12/1969 | Auphan ....................... 607/19 |
| 3,494,369 A | * | 2/1970 | Inoue ........................... 137/13 |
| 3,554,199 A | * | 1/1971 | Auphan ....................... 607/19 |
| 3,563,245 A | * | 2/1971 | McLean et al. ............... 607/35 |
| 3,659,615 A | * | 5/1972 | Enger ........................... 607/35 |
| 3,757,846 A | * | 9/1973 | Herman, Jr. ................ 164/499 |
| 4,175,566 A | * | 11/1979 | Millar ......................... 600/505 |
| 4,453,537 A | * | 6/1984 | Spitzer ....................... 623/3.12 |
| 4,763,646 A | * | 8/1988 | Lekholm ...................... 607/14 |
| 4,925,443 A | * | 5/1990 | Heilman et al. .............. 600/16 |
| 5,674,258 A | * | 10/1997 | Henschel et al. ............. 607/19 |
| 6,033,366 A | * | 3/2000 | Brockway et al. .......... 600/486 |
| 6,486,588 B1 | * | 11/2002 | Doron et al. ................ 310/322 |
| 6,822,343 B1 | * | 11/2004 | Estevez ...................... 290/1 R |
| 6,850,801 B1 | * | 2/2005 | Kieval et al. ................. 607/44 |
| 2005/0113705 A1 | * | 5/2005 | Fischell et al. ............. 600/515 |
| 2005/0136385 A1 | * | 6/2005 | Mann et al. ................. 434/320 |

* cited by examiner

*Primary Examiner*—Julio C. Gonzalez

(57) ABSTRACT

Method and apparatus for generating electrical energy from a subject's body by sensing pulsations of a part of the subject's cardiovascular system and converting such pulsations into electrical energy. In one described preferred embodiment, pulsations of an artery of the subject are sensed and converted. Into electrical energy by utilizing the pulsations to pump liquid with respect to an electrical coil to generate an electrical voltage in the coil. In another described embodiment, pulsations of the heart are sensed; and in a further described embodiment, the pulsations are converted to electrical energy by a piezoelectric device.

13 Claims, 2 Drawing Sheets

METHOD AND APPARATUS FOR BODY GENERATION OF ELECTRICAL ENERGY

RELATED APPLICATION

The present application is related to Provisional Application 60/399,416, filed Jul. 31, 2002, the priority date of which is hereby claimed.

FIELD AND BACKGROUND OF THE INVENTION

The present invention relates to a method, and also to apparatus, for generating electrical energy from a subject's body. Such generated electrical energy may be used, for example, for electrically powering electrical devices implanted in a subject's body, such as cardiac pacemakers, artificial pumps, (e.g., for pumping insulin or other substances), various types of detectors or sensors, and the like.

When an electrical device is implanted in a subject's body, an electrical power supply for powering the implanted device is generally also implanted with the device. However, electrical power supplies have limited lives, and therefore must be either periodically replaced or periodically recharged.

There is an urgent need, therefore, for some means for generating electrical energy from the subject's body itself in order to power such implanted electrical devices.

OBJECTS AND BRIEF SUMMARY OF THE PRESENT INVENTION

An object of the present invention is to provide a method, and also apparatus, for generating electrical energy from a subject's body, which electrical energy may be used for powering or recharging an implanted electrical device.

According to one aspect of the present invention, there is provided a method for powering an implanted mechanical device by generating electrical energy from a subject's body, comprising: physically contacting an external surface of a part of the subject's cardiovascular system and converting with a pulsation transducer to sense pulsations therein and in convert the pulsations into electrical energy; and utilizing the electrical energy to power the implanted device.

According to further features in one described preferred embodiment, the pulsations of the part of the subject's cardiovascular system are converted into electrical energy by utilizing the pulsations to pump a liquid with respect to an electrical coil to generate an electrical voltage in the coil. The liquid is preferably a magnetic liquid, and is pumped in one direction through a closed-loop path enclosed by the electrical coil.

According to further features in the described preferred embodiment, the closed-loop path is at least partly defined by a displaceable member mechanically coupled to the part of the subject's cardiovascular system so as to be cyclically displaced by the pulsations of the part of the subject's cardiovascular system. In the described preferred embodiment, the closed loop path is an annular chamber defined by an outer, circular, stiff wall, and an inner, circular, flexible wall, constituting the displaceable member and mechanically coupled to the pulsating part of the subject's cardiovascular system by loops encircling both the part of the subject's cardiovascular system and the inner, circular, flexible wall. The annular chamber includes one or more one-way valves which permit liquid flow only in one direction around the annular chamber.

According to one described preferred embodiment, the pulsating part of the of the subject's cardiovascular system used for generating the electrical energy is an artery of the subject; and according to a second described embodiment, it is the heart of the subject.

According to a further described embodiment, the pulsations of a part of the subject's cardiovascular system are converted into electrical energy by utilizing the pulsations to drive a piezoelectric device to generate an electrical voltage.

According to another aspect of the present invention, there is provided apparatus for powering an implanted medical device by generating electrical energy from a subject's body, comprising: a transducer constructed so as to be mountable in contact with an external surface of a part of the subject's cardiovascular system for sensing pulsations in the part of the subject's cardiovascular system and for converting the pulsations into electrical energy: and output leads for connecting the output of the transducer to the implanted device.

According to further features in one described preferred embodiment, the transducer device includes a liquid chamber, an electrical coil electromagentically linked to the liquid in the chamber, and a pumping element mechanically coupled to the part of the subject's cardiovascular system so as to be driven by the pulsations thereof to pump the liquid through the chamber and to generate thereby an electrical voltage in the electrical coil.

It will thus be seen that the method and apparatus of the present invention enable electrical energy to be generated within the body itself, which electrical energy may be used for powering or recharging an implanted electrical device, thereby eliminating or reducing the need for periodically recharging or replacing a power supply implanted with the electrical device.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
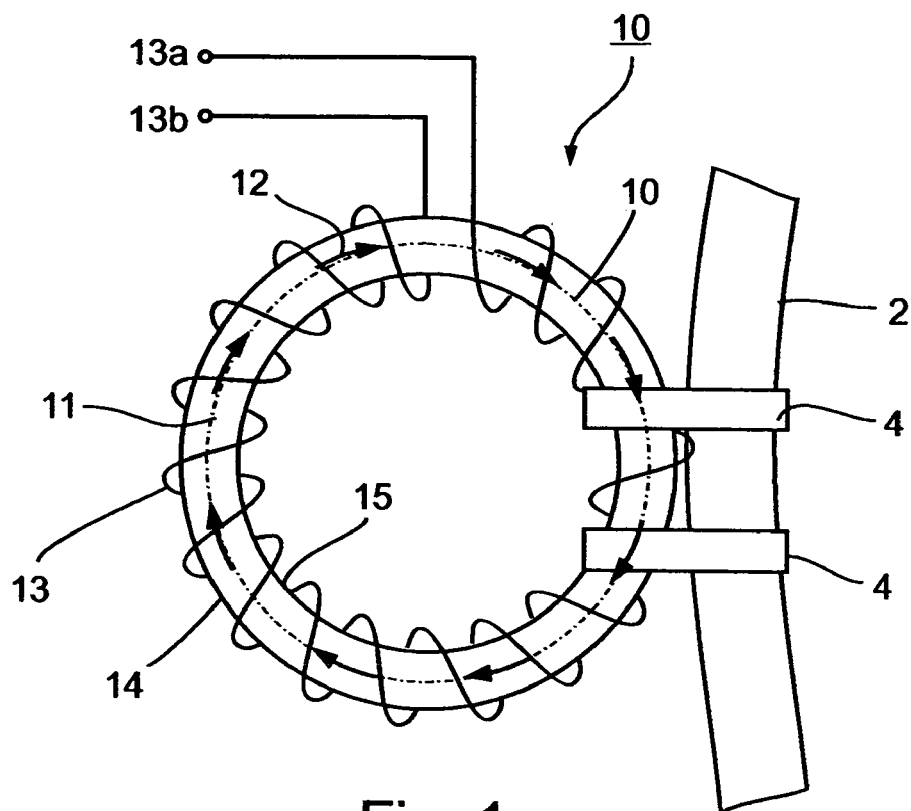
FIG. 1 schematically illustrates one form of apparatus for generating electrical energy from a subject's body by sensing pulsations of an artery of the subject's body and converting such pulsations into electrical energy.
Figure 2:
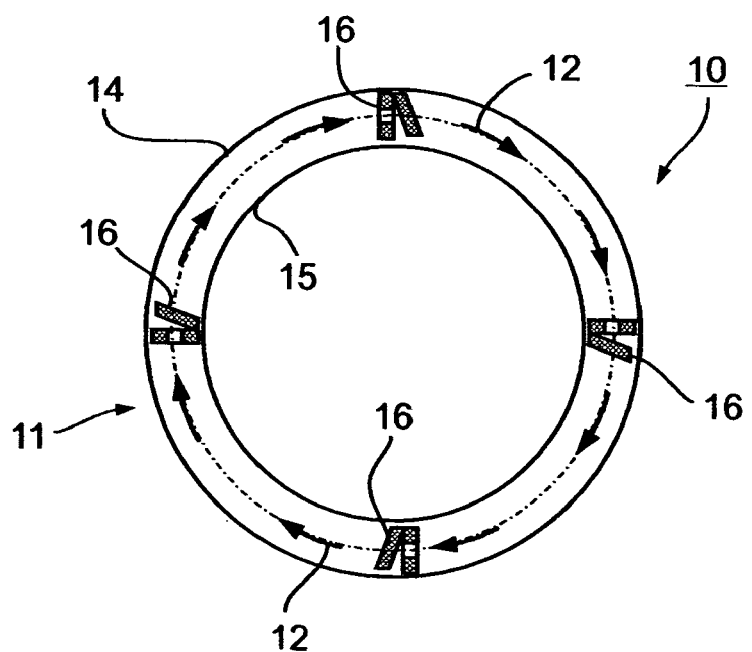
FIG. 2 is an enlarged view more particularly illustrating the construction of the annular chamber used in the apparatus of FIG. 1 for converting the arterial pulsations into an electrical voltage.

In FIGS. 1 and 2 there is illustrated one form of apparatus constructed in accordance with the present invention for generating electrical energy from a subject's body by sensing pulsations of an artery of the subject and converting such pulsations into electrical energy. Thus, FIG. 1 illustrates an artery 2 mechanically coupled by loops 4 to a transducer, generally designated 10, which senses the pulsations of the artery and converts such pulsations into electrical energy.

Transducer 10 illustrated in FIG. 1 includes a liquid chamber 11 of annular configuration containing a magnetic liquid which is caused to flow in one direction, as shown by arrow 12, through the annular chamber 11. Transducer 10 further includes an electrical coil 13 enclosing the annular chamber 11 such that an electrical voltage is generated at the output terminals 13a, 13b of coil 13, as the magnetic liquid is pumped through the annular chamber 11 by the pulsations of the artery 2.

As shown in FIG. 2, the annular closed-loop chamber 11 is defined by an outer circular, stiff wall 14 and an inner, circular, flexible wall 15 which is displaceable towards and away from the stiff wall 14 in order to pump the liquid through the annular chamber. The inner flexible wall 15 is mechanically coupled by the loops 4 to the artery 2, which loops encircle both the artery and wall 15, such that the pulsations of the artery displace the inner wall 15 towards and away from the outer wall 14 to pump the liquid around the annular chamber in the direction of arrow 12. For this purpose, annular chamber 11 includes a plurality of membrane-type one-way valves 16 permitting the liquid flow only in the direction of arrow 12, and thereby producing the one-directional flow of the liquid by the pulsations of the artery 2.

As indicated earlier, electrical coil 13 is would around the annular closed-loop chamber 11, such that the flow of the magnetic liquid in the direction of arrow 12 through the annular chamber generates an electrical voltage in the coil, which voltage appears at its output terminals 13a, 13b.

Figure 3:
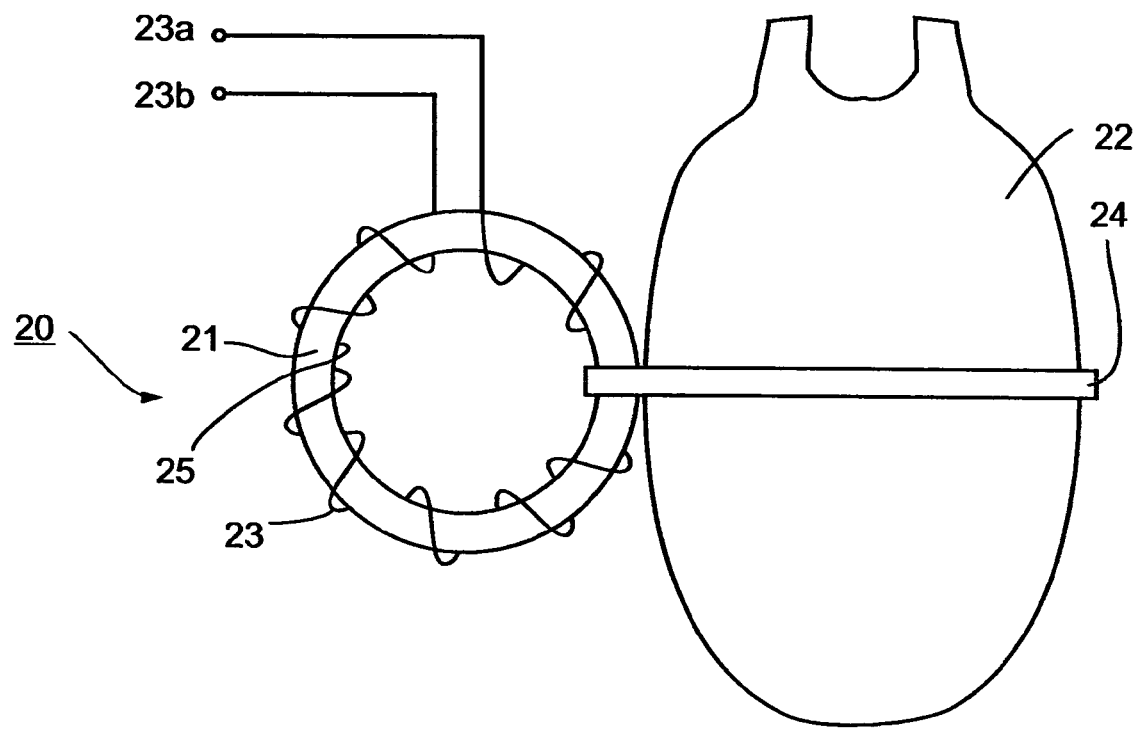
FIG. 3 schematically illustrates an apparatus constructed in accordance with the present invention for sensing pulsations of the subject's heart and converting such pulsations into electrical energy.

FIG. 3 illustrates another embodiment of the invention wherein the electrical transducer, therein generally designated 20, senses pulsations of the subject's heart 22 by means of one or more mechanical loops 24 looping the heart and the inner, circular flexible wall 25, corresponding to wall 15 in FIGS. 1 and 2. Thus, the cyclical displacements of the inner waif 25 of electrical transducer 20 in FIG. 3 also produces a uni-directional flow of the liquid within the annular chamber 21 to generate an electrical voltage in coil 23 having loops enclosing the annular chamber and having output terminals 23a, 23b for outputting the generated valtage.

Figure 4:
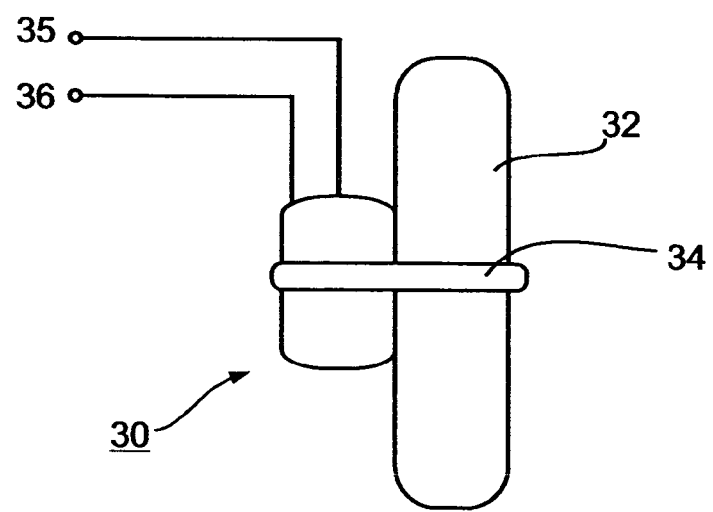
FIG. 4 illustrates another apparatus constructed in accordance with the present invention utilizing a piezoelectric device for sensing pulsations in the subject's artery and for converting such pulsations into electrical energy.

FIG. 4 illustrates a further embodiment of the invention wherein the electrical transducer, therein generally designated 30, is a piezoelectric device which is mechanically coupled to an artery 32 of the subject by mechanical loops 34 so as to sense the pulsations of the artery, and to generate an electrical voltage at the output terminals 35, 36 of the piezoelectric device 30.

As described earlier, the electrical transducers illustrated in FIGS. 1–4 may be implanted in the subject's body and used for supplying power to, or recharging the power supply of, electrical devices implanted into the subject's body, such as a cardiac pacemaker, an artificial pump, a detector or sensor, or the like.

While the invention has been described with respect to several preferred embodiments, it will be appreciated that these are set forth merely for purposes of example, and that many other variations, modifications and applications of the invention may be made.

What is claimed is:

1. A method for powering an implanted medical device by generating electrical energy from a subject's body, comprising:
    physically contacting an external surface of a part of the subject's cardiovascular system with a pulsation transducer to sense pulsations therein and to convert said pulsations into electrical energy;
    and utilizing said electrical energy to power said implanted device;
    said pulsations of the part of the subject's cardiovascular system being converted into electrical energy by utilizing said pulsations to pump a liquid with respect to an electrical coil to generate an electrical voltage in said coil;
    said liquid being pumped in one direction through a closed-loop path enclosed by said electrical coil;
    said closed-loop path being at least partly defined by a displaceable member mechanically coupled to said pulsation transducer physically contacting said external surface of the part of the subject's cardiovascular system so as to be cyclically displaced by said pulsations of said part of the subject's cardiovascular system.

2. The method according to claim 1, wherein said liquid is a magnetic liquid.

3. The method according to claim 1, wherein said closed loop path is an annular chamber defined by an outer, circular, stiff wall, and an inner, circular, flexible wall, constituting said displaceable member and mechanically coupled to said part of the subject's cardiovascular system by one or more loops encircling both said part of the subject's cardiovascular system and said inner, circular, flexible wall.

4. The method according to claim 3, wherein said annular chamber includes one or more one-way valves which permit liquid flow only in one direction around said annular chamber.

5. The method according to claim 1, wherein said part of the subject's cardiovascular system is an artery of the subject.

6. The method according to claim 1, wherein said part of the subject's cardiovascular system is the heart of the subject.

7. The method according to claim 1, wherein said pulsations of a part of the subject's cardiovascular system are converted into electrical energy by utilizing said pulsations to drive a piezoelectric device to generate an electrical voltage.

8. Apparatus for powering an implanted medical device by generating electrical energy from a subject's body, comprising: a transducer constructed so as to be mountable in contact with an external surface of a part of the subject's cardiovascular system for sensing pulsations in said part of the subject's cardiovascular system and for converting said pulsations into electrical energy; and output leads for connecting the output of said transducer to said implanted device;

said transducer including a liquid chamber, an electrical coil electromagentically linked to the liquid in said chamber, and a pumping element mechanically coupled to said part of the subject's cardiovascular system so as to be driven by said pulsations thereof to pump said liquid through said chamber and to generate thereby an electrical voltage in said electrical coil;

said liquid chamber being of a closed-loop configuration and enclosed by said electrical coil; said annular liquid chamber is defined by an outer, circular, stiff wall, and an inner, circular, flexible wall, mechanically coupled to said part of the subject's cardiovascular system by one or more loops encircling both said part of the subject's cardiovascular system and said inner, circular, flexible wall.

9. The apparatus according to claim 8, wherein said liquid is a magnetic liquid.

10. The apparatus according to claim 8, wherein said annular chamber includes one or more one-way valves which permit liquid flow only in one direction around said annular chamber.

11. The apparatus according to claim 8, wherein said transducer is constructed and dimensioned to sense pulsations of an artery of the subject, and to convert such pulsations into electrical energy.

12. The apparatus according to claim 8, wherein said transducer is constructed and dimensioned to sense pulsations of the subject's heart and to convert such pulsations into electrical energy.

13. The apparatus according to claim 8, wherein said transducer is a piezoelectric device.

* * * * *